United States Patent [19]
Katsuda et al.

[11] Patent Number: 5,644,866
[45] Date of Patent: Jul. 8, 1997

[54] BATTERY-ACTUATED INSECTICIDE TRANSPIRATOR AND METHOD FOR TRANSPIRATING INSECTICIDE

[75] Inventors: Yoshio Katsuda, 2-10-10, Kamikoutouen, Nishinomiya-shi, Hyogo-ken; Tsutomu Kanzaki, Takarazuka, both of Japan

[73] Assignee: Yoshio Katsuda, Hyogo-ken, Japan

[21] Appl. No.: 500,245

[22] Filed: Jul. 10, 1995

[30] Foreign Application Priority Data

Jul. 15, 1994 [JP] Japan .................................. 6-194517

[51] Int. Cl.$^6$ ........................................... A01M 13/00
[52] U.S. Cl. ...................................... 43/129; 239/56
[58] Field of Search ................... 43/1, 124, 132.1, 43/125, 129, 131; 239/58, 56; 422/125, 305, 307

[56] References Cited

U.S. PATENT DOCUMENTS

| | | | |
|---|---|---|---|
| 4,037,352 | 7/1977 | Hennart | 43/129 |
| 4,163,038 | 7/1979 | Nishimura | 43/125 |
| 4,214,146 | 7/1980 | Schimanski | 43/129 |
| 4,401,783 | 8/1983 | Kotian | 524/371 |
| 4,771,563 | 9/1988 | Easley | 43/129 |
| 4,860,488 | 8/1989 | Shigetoyo | 43/129 |
| 4,874,789 | 10/1989 | Yamamoto | 514/65 |
| 4,968,487 | 11/1990 | Yamamoto | 422/125 |
| 5,094,025 | 3/1992 | Daniels | 43/129 |
| 5,305,541 | 4/1994 | Simpson | 43/129 |

FOREIGN PATENT DOCUMENTS

| | | | |
|---|---|---|---|
| 0290159 | 11/1988 | European Pat. Off. | 43/132.1 |
| 0174628 | 7/1990 | Japan | 43/131 |
| 2-200137 | 8/1990 | Japan | 43/124 |
| 3072833 | 3/1991 | Japan | 43/124 |
| 6-205634 | 7/1994 | Japan | 43/125 |
| 1366041 | 9/1974 | United Kingdom | 43/129 |

*Primary Examiner*—Joseph J. Hail, III
*Attorney, Agent, or Firm*—Oliff & Berridge

[57] ABSTRACT

A battery-actuated insecticide transpirator comprises: a radiation plate located in contact with an insecticide; and a heating element using a battery; wherein the surface of radiation plate is heated to a temperature of from 90° to 130° C. for transpirating the insecticide, and wherein the heating element consists of a battery connected to a positive temperature coefficient thermistor (an organic PTC) made from a mixture of thermoplastic polyolefin resin and carbon; and wherein the insecticide is a cyclopropane carboxylic ester pyrethroid having a vapor pressure of $1.0 \times 10^{-4}$ mmHg or higher at 2° C. A method for transpirating insecticide using the transpirator.

5 Claims, 3 Drawing Sheets

BATTERY-ACTUATED INSECTICIDE TRANSPIRATOR AND METHOD FOR TRANSPIRATING INSECTICIDE

BACKGROUND OF THE INVENTION

The present invention relates to a battery-actuated insecticide transpirator and a method for transpirating insecticide using the same.

Conventionally, there are known devices for transpirating chemicals such as insecticide impregnated in a mat by heating the mat. Electric mosquito-repellent device is an example of these devices. This type of devices transpirate the insecticides such as allethrin, furamethrin, and prallethrin, which are impregnated into a mat by heating the mat to a temperature ranging from 150° to 180° C. The transpiration sustains for about 12 hours. The device has, however, disadvantage that it is applicable only in indoor service because it requires AC power ranging from 100 to 200 V.

As for the insect-proof agent and insecticide to be used at outdoor where no power cable is available, mosquito-repellent incense has long been used. Mosquito-repellent incense has, however, an inherent problem of existence of fire. Responding to the fire problem, several studies were made to apply what is called "oil-fed pocket warmer" which uses volatile fuel such as benzine, LPG, and solid phase methanol, under the existence of a metallic catalyst for transpirating insecticide. The application of oil-fed pocket warmer, however, failed to bring into practical use because of the toxicity of methanol, the poor safety of volatile fuel against fire, and the difficulty of temperature control.

There was an idea to use dry cells and storage cells instead of AC power source. In that case, no exothermic performance is obtained when dry cells are connected to an inorganic positive temperature coefficient thermistor (inorganic PTC consisting mainly of barium titanate and lead oxide) which has been used as a heating means in the conventional electric mosquito-repellent device actuated by 100 V power source. Regarding the lead storage cells for vehicles, which are only possible candidate for the application, they satisfy the object owing to their ability of recharging during operation. Nevertheless, the use of rechargeable cells is limited to vehicles, and their large capacity is far from general service. In this respect, to utilize dry cells and storage cells, and to sustain a satisfactorily long period of heating, it is required to reduce the temperature of radiation plate from the conventional level (150°–180° C.) to 130° C. or below for reducing the power consumption. Inorganic PTCs, however, cannot reduce their resistance below a certain level, so that they hardly attain the desirable temperature level.

Responding to the above-described problems, the present invention is directed to provide a battery-actuated insecticide transpirator using dry cells and storage cells, in which the temperature of a radiation plate is lowered to a range of from 90° to 130° C. to provide a satisfactory exothermic sustained performance with a cost-feasibility, and to realizes a method for transpirating insecticide using the same.

SUMMARY OF THE INVENTION

To achieve the above-described object, a battery-actuated insecticide transpirator according to the first aspect of the present invention comprises: a radiation plate located in contact with an insecticide; and a heating means using a battery, wherein the surface of the radiation plate is heated to a temperature of from 90° to 130° C. for transpirating the insecticide, wherein the heating means consists of a battery connected to a positive temperature coefficient thermistor (an organic PTC) made from a mixture of thermoplastic polyolefin resin and carbon; and the insecticide is a cyclopropane carboxylic ester pyrethroid having a vapor pressure of $1.0 \times 10^{-4}$ mmHg or higher at 20° C.

According to another aspect of the invention, the total capacity of the battery defined in the first aspect of the invention is set to from 2 to 7 V.

According to further another aspect of the invention, a battery-actuated insecticide transpirator comprises: a radiation plate located in contact with an insecticide; and a heating means using a battery, wherein the heating means consists of a battery connected to a positive temperature coefficient thermistor (an organic PTC) made from a mixture of thermoplastic polyolefin resin and carbon to heat the surface of radiation plate to a temperature of from 90° to 130° C. to transpirate a cyclopropane carboxylic ester pyrethroid having a vapor pressure of $1.0 \times 10^{-4}$ mmHg or higher at 20° C.

DETAILED DESCRIPTION OF THE PREFERRED EMBODIMENTS

According to the configuration of the first aspect of the present invention, the heating means uses an organic PTC consisting of a mixture of thermoplastic polyolefin resin and carbon instead of an inorganic PTC which is used in the conventional electric mosquito-repellent device powered by 100 V power source. As a result, the temperature of the radiation plate for transpirating insecticide can be set at a range of from 90° to 130° C. In concrete terms, inorganic PTCs cannot reduce the resistance to a desired level, but organic PTCs of the present invention have a characteristic that can reduce the resistance to a satisfactorily low level. Accordingly, with the application of pyrethroid having a specific vapor pressure, the present invention provides a high performance battery-actuated insecticide transpirator.

Figure 3:
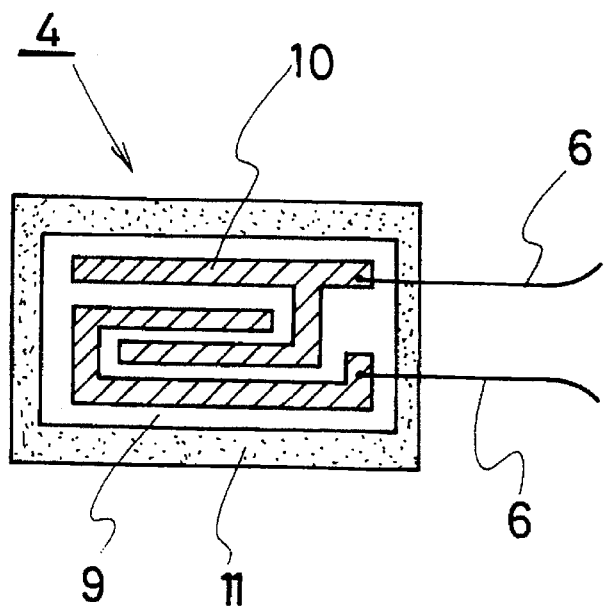
FIG. 3 shows a plan view of one example of organic PTC used in the battery-actuated insecticide transpirator of the invention.
Figure 4:
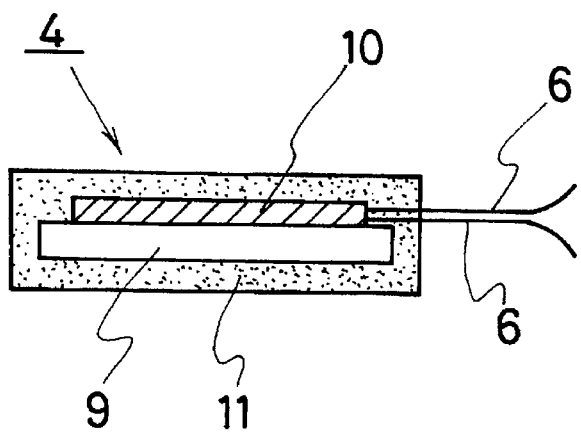
FIG. 4 shows a front cross sectional view of one example of organic PTC used in the battery-actuated insecticide transpirator of the invention.

The thermoplastic polyolefin resin may be polyethylene resin or polypropylene resin, but is not limited to those resins, and the mixing rate of carbon is also arbitrarily determined depending on the use object. A wide variety of shapes are available for organic PTCs. Examples of the shape of organic PTC of the invention are shown in FIGS. 3 and 4, where a layered organic PTC composition consisting of a mixture of polyolefin resin and carbon is connected to a copper electrode plate, which composition is covered with an insulator such as flame-retardant polyester on both sides thereof to form a shape of 10×15 mm. By applying 2 to 7 V to the composition using dry cells, the current of about 100 to 400 mA and the heating temperature of from about 90° to 130° C. are obtained. These heating characteristics are arbitrarily selected. Normally, a radiation plate used as the conduction material for the heat source and as the pan for the insecticide is attached to the organic PTC. The shape of the radiation plate is not specifically limited, too.

The battery used in the invention is either a dry cell or a rechargeable storage cell, and commercial products are applicable. Examples of dry cell include alkali cell, manganese cell, lithium cell, mercury cell, and silver oxide cell. Examples of rechargeable storage cell include nickel-cadmium cell, nickel-zinc cell, sodium-sulfur cell, and lead cell. Other type of cells are also applicable.

Since the insecticide transpirator of the invention sets the temperature of radiation plate in a range of from 90° to 130° C., a preferred insecticide to be applied to the device is a cyclopropane carboxylate ester pyrethroid which has a vapor pressure of $1.0 \times 10^{-4}$ mmHg or higher at 20° C. Typical examples of that type of pyrethroids are given below. Needless to say, the types of applicable pyrethroids are not limited to those listed below. In addition, if the pyrethroid contains an optical isomer on the basis of asymmetric carbon in acid or alcohol part, or contains a geometric isomer, the sole isomer or an arbitrary mixture thereof may be included in the insecticide of the present invention.

A) 1-ethynyl-2-methyl-2-pentenyl chrysanthemate (hereinafter referred to simply as "empenthrin")

B) 5-propargyl-2-furylmethyl chrysanthemate (hereinafter referred to simply as "furamethrin")

C) 5-propargyl-2-furylmethyl 2,2,3,3-tetramethylcyclopropane carboxylate (hereinafter referred to simply as "compound C")

D) 2-methyl-4-oxo-3-propargyl-2-cyclopentenyl 2,2,3,3-tetramethylcyclopropane carboxylate (hereinafter referred to simply as "compound D")

E) 5-propargyl-2-methyl-3-furylmethyl 2,2,3,3-tetramethylcyclopropane carboxylate (hereinafter referred to simply as "compound E")

F) 2,3,5,6-tetrafluorobenzyl 3-(2,2-dichlorovinyl)-2,2-dimethylcyclopropane carboxylate (hereinafter referred to simply as "compound F")

G) 2,3,5,6-tetrafluorobenzyl chrysanthemate (hereinafter referred to simply as "compound G")

H) 2,3,4,5,6-pentafluorobenzyl 3-(2,2-dichlorovinyl)-2,2-dimethylcyclopropane carboxylate (hereinafter referred to simply as "compound H")

These insecticides normally contain stabilizer such as BHT, DBH, BHA, and Yoshinox 425, volatilization adjuster, fragrance, coloring matter, and solvent such as petroleum, at an adequate amount. Furthermore, they may contain other chemicals such as fungicide, anti-microbial agent, acaricide, and deodorant, at need, to prepare a multi-functional composition.

According to another configuration of the invention, since the total capacity of the battery of the insecticide transpirator is 2 to 7 V, it allows an easy operation and gives sufficient performance. For example, when two alkali cells each having a capacity of 1.5 V are connected in series, the heating temperature of from 90° to 130° C. is maintained for 6 to 8 hours. If two sets of a pair of the cells are connected in parallel, then the operating hours is extended to 12 to 16 hours.

According to further another configuration of the invention, a useful method for transpirating insecticide using the insecticide transpirator defined in the first aspect of the invention may be provided. Normally, an insecticide is placed in contact with the radiating plate, however, various methods can be employed as a means to make contact with each other. For example, there is a method what is called the "mosquito-repellent mat system" in which the insecticide solution is impregnated into a mat made of pulp or linter using an adegmate quantitative-charging device, or what is called the "barbecue system" in which the radiation plate is formed in a vat shape to which the insecticide or its solution is directly charged, or what is called the "suck-up system" in which an adequate liquid-sucking wick is used to suck-up the insecticide solution while contacting the tip of the liquid-sucking wick to the heating plate. Among these, the mosquito-repellent mat system is most preferable.

When an insecticide is applied to the radiation plate positioned at upper part of the insecticide transpirator of the invention, and the organic PTC which is a characteristic of the invention is connected to the dry cell or the rechargeable storage cell built-in the transpirator to heat the radiation plate to a temperature of from 90° to 130° C., the insecticide vaporizes with the elapse of time to sustain the strong effect of insecticide and insect-proof over a wide range for a long period. Accordingly, the present invention provides a highly practical battery-actuated insecticide transpirator which can be easily operated even at outdoor owing to its battery-actuation system and which is cost effective, and also provides a method for transpirating the insecticide.

The shape and size of the insecticide transpirator of the invention can be arbitrarily designed, and as well as the conventional electric mosquito-repellent device, the transpirator according to the invention may include switch, power indication lamp, mat holding member, or the like, at need, in addition to the essential components of radiation plate, organic PTC, and battery.

To make clear the superiority of the insecticide transpirator and the method for transpirating the insecticide according to the invention, the detailed description is made with reference to the following embodiments and test examples.

EXAMPLE 1

Figure 1:
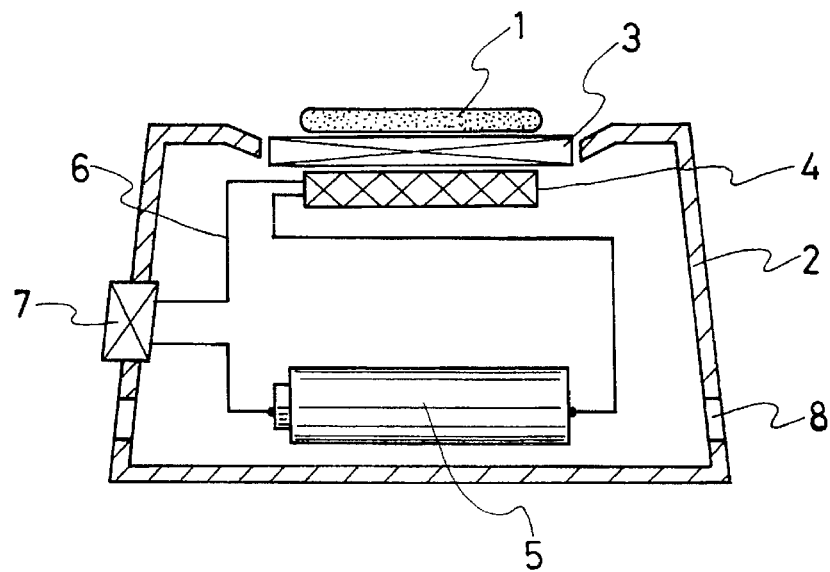
FIG. 1 shows a cross sectional view of the battery-actuated insecticide transpirator of one example of the invention

FIG. 1 shows an example of the insecticide transpirator of the invention. Reference numeral 1 denotes a pulp mat having a size of 1.1×1.6 cm and 1 mm in thickness, into which cyclopropane carboxylic ester pyrethroid having a vapor pressure not less than $1.0 \times 10^{31\ 4}$ mmHg at 20° C. is impregnated. Reference numeral 2 denotes a body casing of the transpirator which includes a radiation plate 3 which receives the mat 1, an organic PTC 4 which heats the radiation plate 3, and a battery 5. Reference numeral 6 denotes a wiring and reference numeral 7 denotes a switch. Further, the body casing 2 is provided with a vent 8 at the bottom, through which air enters and passes through inside space of the body casing 2 and ascends inside thereof to enhance the volatilization of the insecticide component.

Incidentally, the organic PTC 4 has a configuration, for example, illustrated in FIG. 3 (plan view) and FIG. 4 (front sectional view).

Reference numeral 9 denotes an organic PTC composition 9; 10, a copper electrode plate; and 11, an insulator. The structure of the transpirator is not specifically limited to the one given in the example, and various types of configurations and shapes are applicable.

With the transpirator having the configuration given above, a mat 1 containing 40 mg of compound F was placed on the radiation plate 3, and two alkali dry cells each having a unit capacity of 1.5 V were connected in series and two sets of one pair of the alkali dry cells were connected in parallel. As a result, the temperature of the radiation plate could be maintained at about 100° C. for about 15 hours, and the transpirator was effective to repel mosquitoes for two days.

EXAMPLE 2

Figure 2:
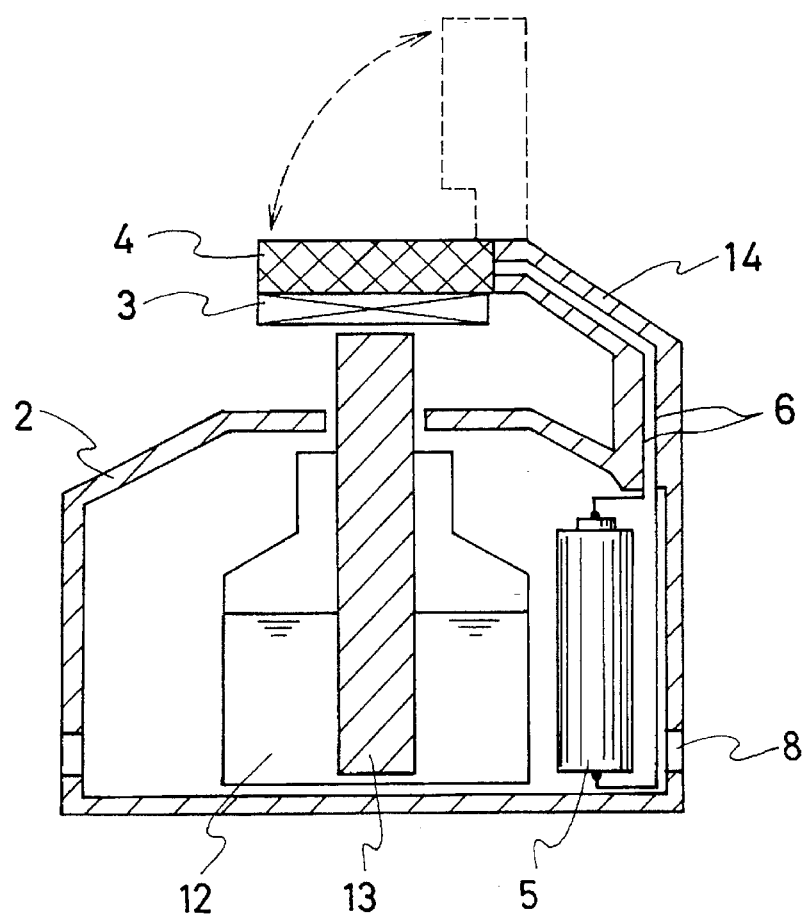
FIG. 2 shows a cross sectional view of the battery-actuated insecticide transpirator of another example of the invention.

FIG. 2 shows another example of the insecticide transpirator according to the invention. Reference numerals 2 through 8 are commonly used as those for Example 1. Reference numeral 12 denotes a bottle to contain the insecticide solution, and the center of which is provided with a liquid-sucking wick 13. An exothermic section including the radiation plate 3 and the organic PTC 4 is supported by the body casing 2 via a mating piece 14 which is freely bent and folded. At the start of use, the heating plate 3 is moved so as to contact with the tip of the liquid-sucking wick 13.

With the transpirator having a configuration given above, a chemical solution containing 1.5% of compound C was used, and a dry cell having a capacity of 10 V was connected. As a result, the transpirator maintained the exothermic temperature at about 110° C. for 12 hours or more. The volatilization of the compound C was a sufficient amount to repel mosquitoes.

Figure 5:
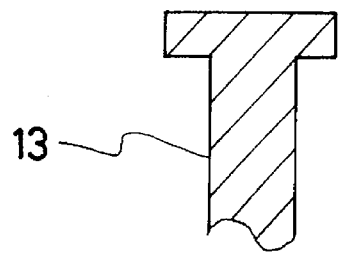
FIG. 5 shows a cross sectional view of a liquid-sucking wick used in the battery-actuated insecticide transpirator of the invention.
Figure 6:
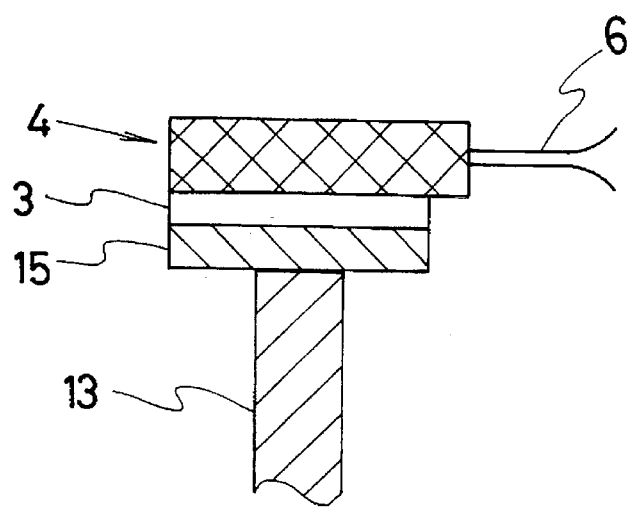
FIG. 6 shows a cross sectional view of a liquid-sucking wick and a liquid-sucking base material used in the battery-actuated insecticide transpirator of the invention.
Figure 7:
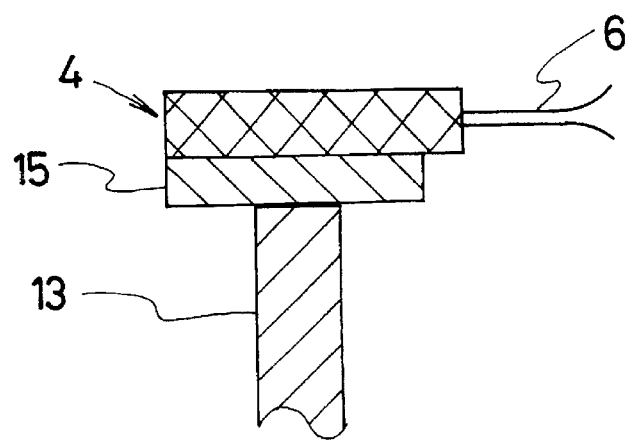
FIG. 7 shows a cross sectional view of a liquid-sucking wick and a liquid-sucking base material used in the battery-actuated insecticide transpirator of the invention.

To widen the volatilization area of the solution of insecticides, the liquid-sucking wick 13 may be formed in a shape illustrated in FIG. 5. Moreover, a liquid-sucking base material 15 made of cloth, paper or thin felt, consisting of natural fiber or synthetic fiber, may be directly attached to the radiation plate 3 or the organic PTC 4 as illustrated in FIGS. 6 and 7.

EXAMPLE 3

Two transpirators each having similar configuration with Example 1 were used. For each of them, a pulp mat having a size of 1.1×1.6 mm and 1 mm in thickness was impregnated with 40 mg of empenthrin. Two alkali dry cells each having a unit capacity of 1.5 V were connected in series and two sets of one pair of alkali dry cells were connected in parallel.

Each of two transpirators was placed at a 2 m distance in a bush of a park where plenty of mosquitoes emerged. A person was made to stand at the middle of these two transpirators to count the number of stings in every 4 min.

As a result, almost no sting was found during about 8 hours of the test in the case where the transpirators according to the invention were used. On the contrary, in a control zone where no transpirator was applied, the person suffered more than 3 stings in every 4 min.

TEST EXAMPLE 1

With the insecticide transpirator described in Example 1, the following volatilization test and potency test were conducted while varying the kind of insecticide and the surface temperature of the radiation plate.

1) Volatilization test . . . The insecticide component volatilized from mat was trapped in a predetermined interval to determine the volatilization rate of the insecticide component per hour: (mg/H).
2) Potency test . . . A transpirator was placed at the center of the bottom floor of a chamber having a size of 2×2×2 m. The potency against the mosquitoes in. a cage placed at an upper corner was determined. The result is summarized in Table 1.

TABLE 1

| | Test condition | | Test result | | | | |
| --- | --- | --- | --- | --- | --- | --- | --- |
| | | Surface | Volatilization (mg/H) | | | Efficiency | | |
| Insecticide (40 mg) | | temperature of radiation plate (°C.) | Immediately after starting volatilization | After 8 hours | After 16 hours | Immediately after starting volatilization | After 8 hours | After 16 hours |
| Transpirator of the Invention | | | | | | | | |
| 1 Empenthrin | | 105 | 1.3 | 1.0 | 1.0 | O | O | O |
| 2 d-T80-furamethrin | | 130 | 1.0 | 0.9 | 0.8 | O | O | O |
| 3 Compound C | | 115 | 1.2 | 1.0 | 0.9 | O | O | O |
| 4 Compound D (alcohol; d-type) | | 120 | 1.0 | 0.9 | 0.8 | O | O | O |
| 5 Compound E | | 120 | 1.1 | 1.0 | 0.9 | O | O | O |
| 6 Compound F | | 110 | 1.1 | 0.9 | 0.9 | O | O | O |
| 7 Compound G | | 90 | 1.0 | 0.9 | 0.8 | O | O | O |
| 8 Compound H | | 95 | 1.0 | 0.9 | 0.8 | O | O | O |
| Comparative Example | | | | | | | | |
| 1 Empenthrin | | 70 | 0.7 | 0.5 | 0.4 | Δ | Δ | Δ |
| 2 Empenthrin | | 140 | 2.4 | 0.4 | <0.1 | O | Δ | X |
| 3 dl, d-T80-allethrin | | 110 | 0.2 | 0.2 | 0.1 | X | X | X |
| 4 d, d-T80-prallethrin | | 120 | 0.2 | 0.1 | 0.1 | X | X | X |

The insecticides Used in the invention effectively volatilized in a temperature of the surface of the radiation plate of the transpirator from 90° to 130° C., and maintained a high potency to mosquitoes for 16 hours. If these insecticides were used at a temperature below 90° C., then the volatility was poor. If the temperature was increased to about 140° C., then the component completely volatilized in a short period, and the sustained performance could not be obtained. Allethrin and prallethrin gave a low vapor pressure of $4.2 \times 10^{-5}$ mmHg and $3.5 \times 10^{-5}$ mmHg at 20° C., respectively, and they could not give an effect of insecticide within a temperature of from 90° to 130° C.

Therefore, the present invention was completed by the combination of various conditions including the use of battery, use of organic PTC to decrease the surface temperature, and selection of insecticide suitable for the temperature range.

According to the present invention, there are provided a practical battery-actuated insecticide transpirator which effectively volatilize the insecticide component in a temperature of from 90° to 130° C. by adopting an organic PTC as the heating means consisting of a mixture of thermoplastic polyolefin resin and carbon, and by applying cyclopropane carboxylic ester pyrethroids having a vapor pressure of $1.0 \times 10^{-4}$ mmHg or more at 20° C., and a method for transpirating insecticide using the same.

What is claimed is:

1. A battery-actuated insecticide transpirator comprising:

a radiation plate located in contact with an insecticide; and a heating means using a battery, wherein the surface of the radiation plate is heated to a temperature of from 90° to 130° C. for transpirating the insecticide, wherein the heating means consists of a battery connected to a positive temperature coefficient thermistor comprising:
   (i) a mixture of thermoplastic polyolefin resin and carbon, (ii) an electrode plate, and (iii) an insulator; and the insecticide is a cyclopropane carboxylic ester pyrethroid having a vapor pressure of $1.0 \times 10^{-4}$ mmHg or higher at 20° C.

2. A battery-actuated insecticide transpirator according to claim 1, wherein the total capacity of the battery contained therein is set to from 2 to 7 V.

3. A transpirator according to claim 1, wherein the vapor pressure is higher than $1.0 \times 10^{-4}$ mmHg at 20° C.

4. A method for transpirating insecticide comprising:

using a battery-actuated insecticide transpirator consisting of a radiation plate located in contact with an insecticide and a heating means using a battery, wherein the heating means consists of a battery connected to a positive temperature coefficient thermistor comprising:
   (i) a mixture of thermoplastic polyolefin resin and carbon, (ii) an electrode plate, and (iii) an insulator, to heat the surface of the radiation plate to a temperature of from 90° to 130° C. to transpirate a cyclopropane carboxylic ester pyrethroid having a vapor pressure of $1.0 \times 10^{-4}$ mmHg or higher at 20° C.

5. A method according to claim 4, wherein the vapor pressure is higher than $1.0 \times 10^{-4}$ mmHg at 20° C.

* * * * *